United States Patent [19]

Glantschnig et al.

[11] Patent Number: 4,934,818
[45] Date of Patent: Jun. 19, 1990

[54] REFRACTIVE INDEX PROFILING TECHNIQUE

[75] Inventors: Werner J. Glantschnig, Belle Mead; Knut D. Pohl, Flemington, both of N.J.

[73] Assignee: American Telephone and Telegraph Company, New York, N.Y.

[21] Appl. No.: 328,412

[22] Filed: Mar. 24, 1989

[51] Int. Cl.⁵ .............................................. G01N 21/41
[52] U.S. Cl. ..................................... 356/73.1; 356/128
[58] Field of Search .............................. 356/73.1, 128

[56] References Cited

U.S. PATENT DOCUMENTS

| 4,227,806 | 10/1980 | Watkins | 356/73.1 |
| 4,726,677 | 2/1988 | Glantschnig et al. | 356/73.1 |

FOREIGN PATENT DOCUMENTS

| 60242 | 4/1982 | Japan | 356/73.1 |
| 155933 | 7/1986 | Japan | 356/73.1 |

OTHER PUBLICATIONS

Saekeang et al., *Applied Optics*, vol. 19, No. 12, Jun. 15, 1980, pp. 2025–2030.
Young, *Applied Optics*, vol. 19, No. 15, Aug. 1, 1980, pp. 2479 and 2480.

*Primary Examiner*—F. L. Evans
*Attorney, Agent, or Firm*—James J. Trainor

[57] ABSTRACT

A monochromatic light beam scans a silica reference and a translucent body, both submerged in index matching fluid and the deflection angle of the beam is measured as it exits the reference, the translucent body and the fluid. This deflection angle of the light beam exiting the reference is compared with the undeflected beam passing through only the fluid. The difference, if any, is used to offset the measurements of the deflection angles of the light beam exiting the translucent body to correct them so that the profile is referenced to the index of silica.

14 Claims, 8 Drawing Sheets

REFRACTIVE INDEX PROFILING TECHNIQUE

TECHNICAL FIELD

This invention relates to a method and apparatus for profiling the refractive index of a fiber optic preform, or other translucent body having an unknown graded or step profile of interest, relative to the refractive index of a reference having a known index of refraction, and more particularly, to a nondestructive method and apparatus for profiling the refractive index of an unclad fiber optic preform or component of a preform relative to the refractive index of a silica reference.

BACKGROUND OF THE INVENTION

Optical fiber is produced by drawing the fiber from a preform. The refractive index profile of the drawn fiber is substantially the same as the profile of the preform from which it is drawn. Deviations from the desired refractive index existing in the preform will thus be repeated in the fiber and may result in unacceptable transmission characteristics. It is therefore prudent to profile the refractive index of the preform before drawing fiber from it to avoid wasting time and money producing worthless scrap.

Historically, refractive index profile measurements have been relative index measurements; the refractive index of the fiber core relative to the doped or undoped silica cladding. It is this relative difference which gives an optical fiber its light guiding properties.

As currently practiced, the manufacture of single mode preforms comprising a core and a clad by the "modified chemical vapor deposition" (MCVD) process has associated cost penalties. This process requires many depressed cladding layers to be built up before the core layers are deposited. These depressed cladding layers are needed to obtain the proper core-to-clad ratio and acceptable loss.

A more economical alternative preform manufacturing technique uses high purity fluorinated silica tubes as starting substrates for MCVD together with rod-in-tube technology as described in U.S. patent application, Ser. No. 099,441, Continuation under Rule 60 of Ser. No. 856,739, filed on Sept. 23, 1987 in the names of J. W. Baumgart et al and assigned to AT & T Technologies, Inc., which is now U.S. Pat. No. 4,820,322 issued on Apr. 11, 1989. By starting with fluorinated tubes the deposition of many fewer depressed cladding layers are required, rendering MCVD more competitive.

The above alternative, as well as others that are being used such as the "outside vapor deposition" (OVD) process, could present profiling problems that current generation preform profilers would not be able to handle.

In the OVD process, the glass precursor vapor is introduced into a hydrolyzing flame and particulate material is formed. This material emanating from the flame is directed toward a mandril on which it is deposited. Following such deposition, the deposited material is consolidated into a transparent glass, the mandril removed and the resultant hollow tube collapsed to form a solid, cylindrical optical fiber preform which may not have a silica cladding.

The current method and apparatus for nondestructively determining the refractive index profile of an optical fiber preform have been disclosed in U.S. Pat. No. 4,227,806 granted to Lawrence S. Watkins (incorporated by reference herein). This approach works well with a preform having a core and a silica clad. However, prior art apparatus is not capable of accurately profiling the refractive index of an unclad preform, or component of a preform relative to silica or another reference.

Prior art apparatus is shown schematically in FIG. 1. Tank 10 has heads 11 and 12 supporting side windows 13 and 14. A preform 15 having a core 16 and cladding 17 is suspended in a fluid such as index matching oil 18 with its longitudinal axis parallel to the plane of windows 13 and 14 by a support (not shown).

Oil 18 with its index of refraction close to that of cladding 17 is usually used instead of air when accuracy is required to avoid unpredictable variations in the refraction of beam 19 caused by non-circularity of the surface of cladding 17.

In operation, a narrow monochromatic beam of light 19 from light source 20, focused at the center of core 16, is scanned across preform 15 such that beam 19, as it scans, is always substantially perpendicular to a plane containing the longitudinal axis of preform 15. The refraction angle of beam 19 exiting preform 15 is detected by detector 21. A computer 22 programmed to process the detected data constructs the refractive index profile and displays it by employing an output device such as plotter 23.

In the case of a fluorinated silica tube to be used as a substrate for MCVD, there is a need to profile the down-doped tubes as part of an initial quality check. Again, however, there is no silica reference without which the amount of fluorine down-doping could not be reliably measured. A silica jacket could be collapsed over an unclad object, such as a fluorinated tube or an OVD preform, in order to accurately measure its index depression relative to silica. This, of course, would be a time-consuming, inefficient and wasteful test procedure. Destructive tests, such as slicing and direct analysis could also be employed with obvious disadvantages.

It was also attempted to use index matching oil 18 as a surrogate for the silica cladding, but for reasons that will be discussed hereinafter, this procedure does not provide accurate results.

Thus, there is a need for an efficient, accurate and nondestructive method and apparatus for constructing, relative to silica, the refractive index profiles of unclad preforms, unclad components of preforms and other unclad transparent bodies.

SUMMARY OF THE INVENTION

The instant invention solves the foregoing problem with a method and apparatus which allows the construction of the refractive index profile of a translucent body, such as an unclad preform or component of a preform, by scanning the translucent body and a reference having a known index of refraction, such as a silica rod, with a narrow beam of monochromatic light, detecting the refraction angles of the beam exiting both the translucent body and the reference and processing the detected refraction angle data to enable the profile with the desired reference to be constructed. These and other objects, features and advantages will be better understood from a consideration of the following detailed description taken in conjunction with the accompanying drawings.

DETAILED DESCRIPTION

The present invention is explained in the context of nondestructively constructing the index of refraction profile of an unclad optical fiber preform, or component of a preform, relative to the refractive index of a reference such as fused silica. However, such description is for purposes of exposition and not for limitation. Unclad preforms and other objects, such as a graded index rod (GRIN) lenses having index profiles which are graded, step or otherwise, could be profiled and other parameters susceptible of being determined with the detected data could be computed.

Figure 1:
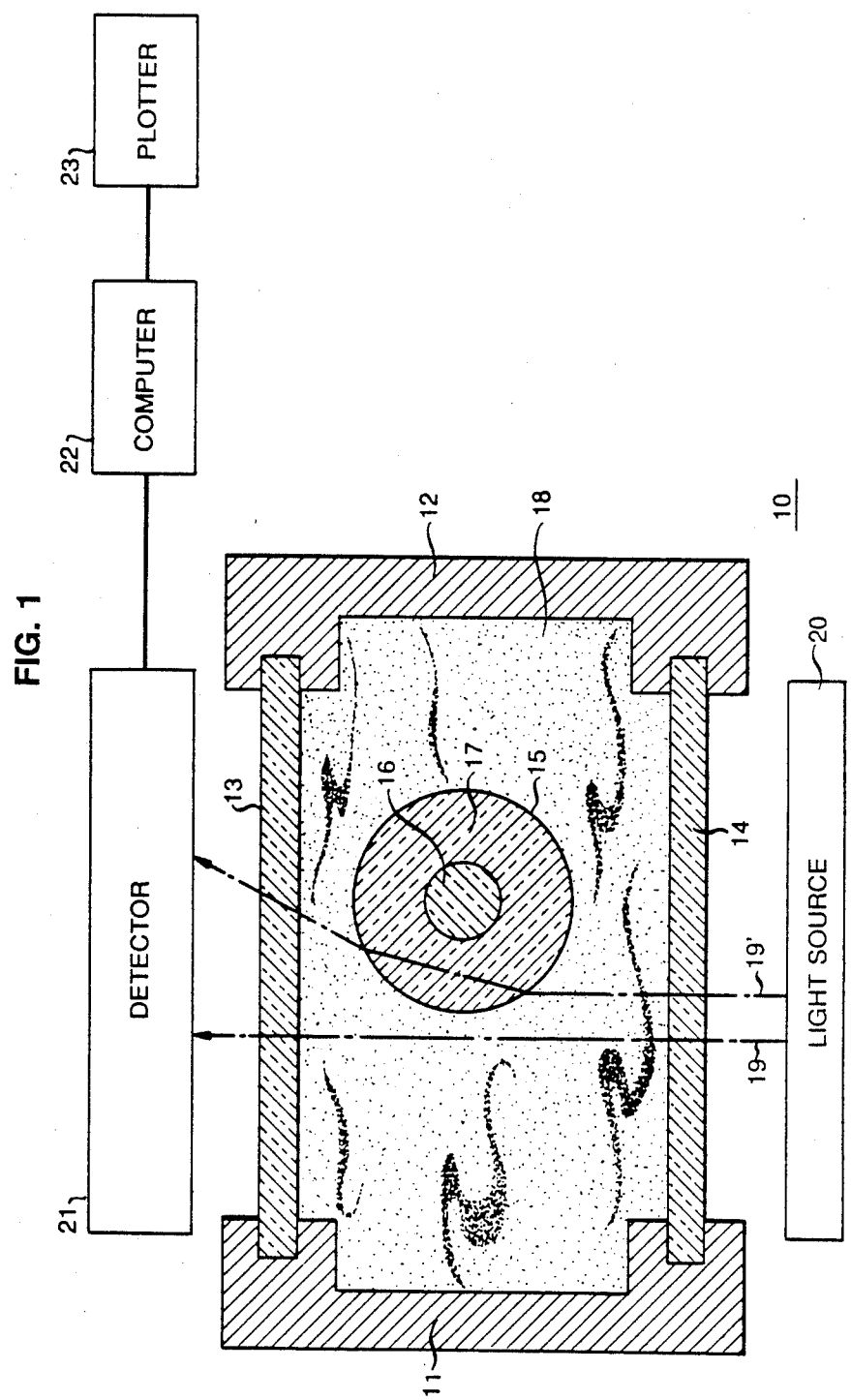
FIG. 1—block schematic representation of a prior art apparatus for profiling the refractive index of a clad preform.
Figure 2:
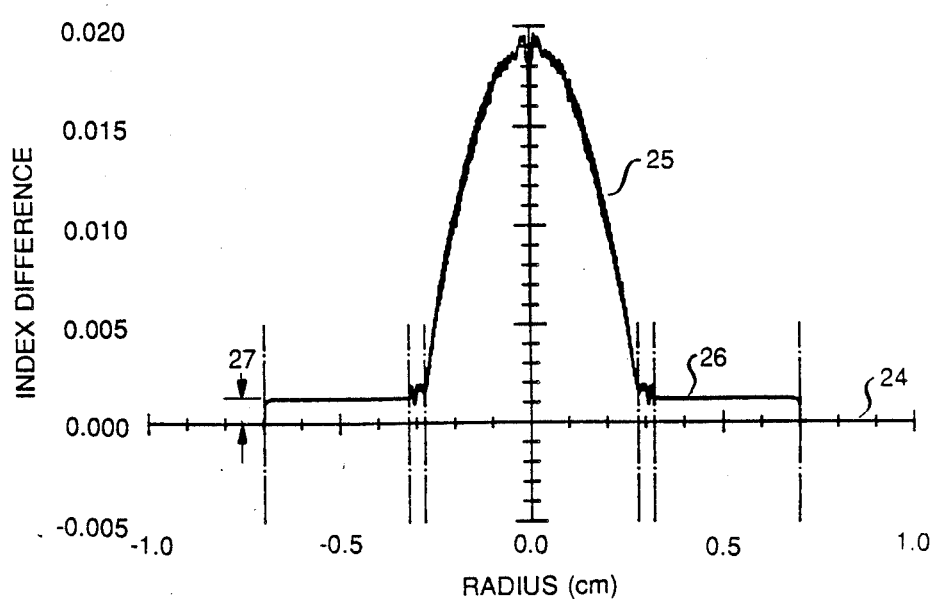
FIG. 2—refractive index profile of a multi-mode preform.

FIG. 2 shows the index profile of a multi-mode clad preform. The prior art method used simply consists of reconstructing the profile of the whole preform including its cladding. By this method the profile is referenced to the index 24 of index matching fluid 18 in preform tank 10. However, since the cladding is explicitly included in the profile, it is clear by how much the core index 25 varies from the clad index 26.

Scanning collimated light beam 19 across preform 15 does not take significant time. However, computer processing time can be appreciable. Hence, it is usually preferable to preprocess the refraction angle data and then reconstruct the profile. The preprocessing step corrects the data for any index mismatch 27 between fluid 18 and cladding 17. If there is no mismatch 27 between index oil 18 and cladding 17, beam 19 will pass straight through without being refracted. On the other hand, the refraction due to any mismatch 27 can be detected and preprocessed by computer 22 to eliminate its effect in plotting the profile.

Figure 3:
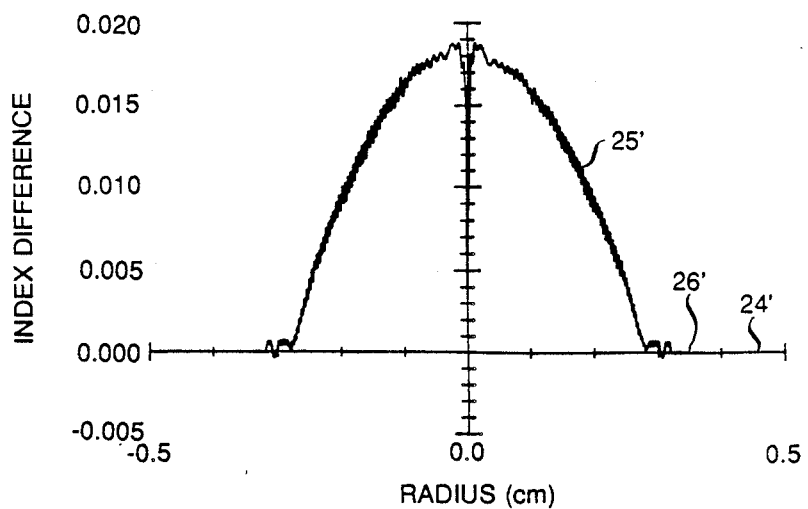
FIG. 3—preprocessed refractive index profile of the multi-mode preform of FIG. 2.
Figure 4:
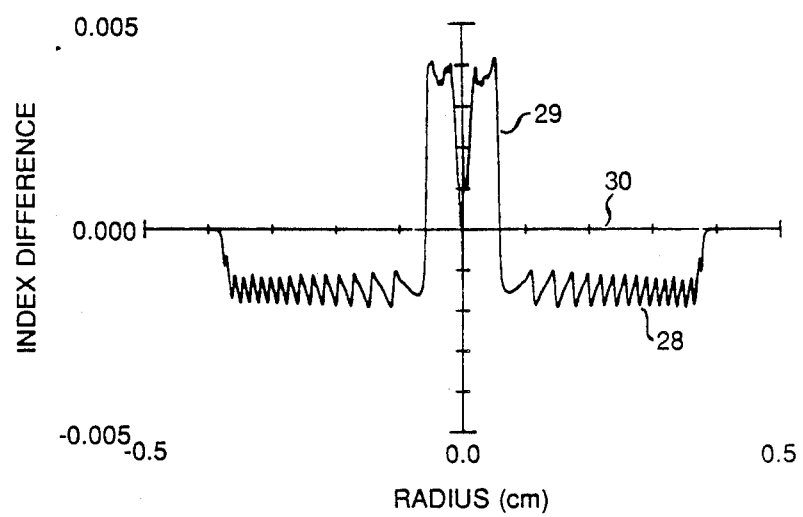
FIG. 4—preprocessed refractive index profile of a single mode preform with a depressed clad.

Referring to FIGS. 3 and 4, this correction accomplishes two functions. First, as shown in FIG. 3 for the multi-mode fiber of FIG. 2, it enables the profile reconstruction to be truncated near the core-clad interface thereby saving processing time. Profiling the entire clad conveys no additional information. Second, preprocessing automatically references the reconstructed core profile to the index of the cladding.

FIG. 4 shows a preprocessed refractive index profile of a single mode depressed clad preform. The depressed clad index 28 and the core index 29 are both referenced to the refractive index 30 of the pure silica clad.

A slight index mismatch 27 between index oil 18 and cladding 17 is often useful in precisely locating the surface of cladding 17 as beam 19 would be deflected as it enters and exits cladding 17.

In any event, it would not be very practical in a manufacturing environment to attempt to keep the refractive index of oil 18 precisely matched to the index of cladding 17 as the refractive index of index matching oil 18 is a relatively sensitive function of temperature compared with the index of silica which is the usual material of cladding 17.

Figure 5:
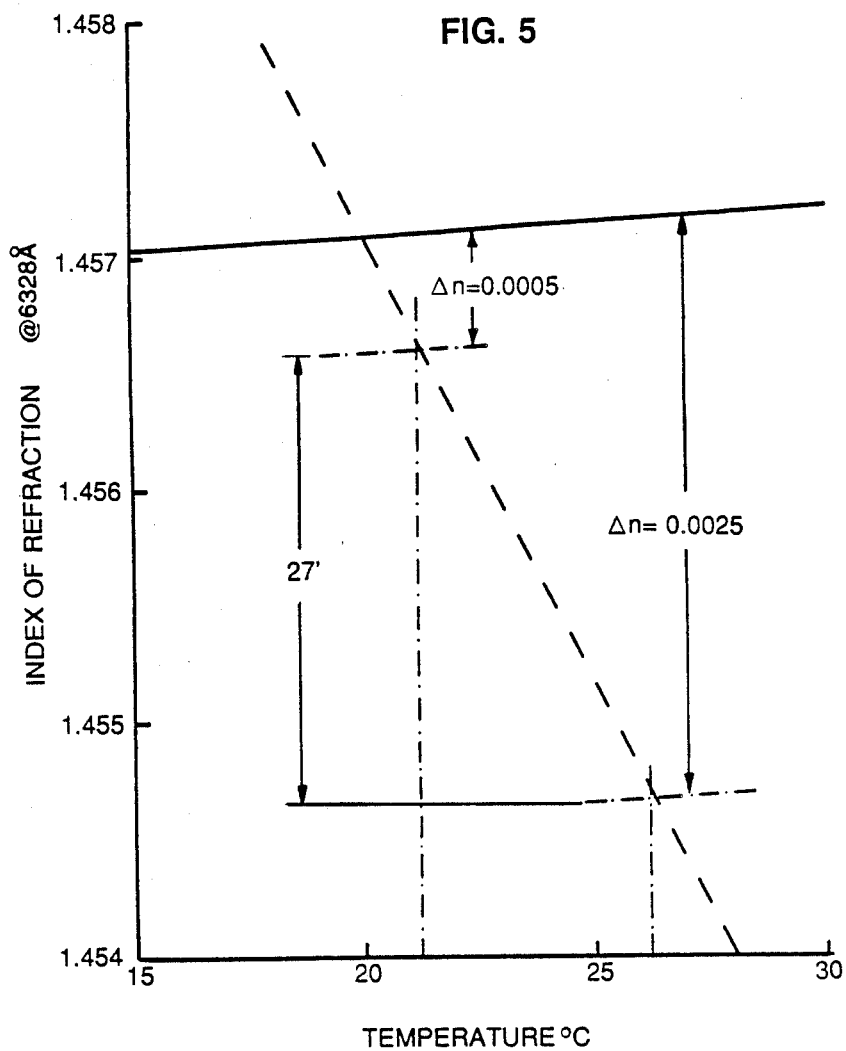
FIG. 5—plot of indexes of refraction of index matching oil and silica will change in temperature.

Referring to FIG. 5, it can be seen that even over a range of 5° C. the index mismatch 27' between the index matching oil and the silica varies by as much as 0.002 which is quite significant.

It is readily seen that the prior art apparatus would not be capable of profiling the refractive index of a body relative to a silica reference if the object did not have a silica clad. However, this is precisely the problem that was confronted when it was attempted to profile the refractive index of preform components to be used in the rod-in-tube process previously mentioned.

Absolute refractive index measurements could be made if a surrogate silica reference could be substituted for the silica cladding. In this regard, the linearity of the change of the index of refraction of oil with change in temperature, as shown in FIG. 5, suggests an oil index determination scheme based on an on-line oil temperature measurement technique. However, as previously mentioned, it turns out there are several problems with this approach. The most important problem is that the oil index cannot be computed precisely enough. Furthermore, the oil index may be affected by contaminants that build up in the preform tank over time, and there is even some question about the long term stability of the oil itself. None of these factors are addressed by simply measuring the temperature of the oil.

Figure 6:
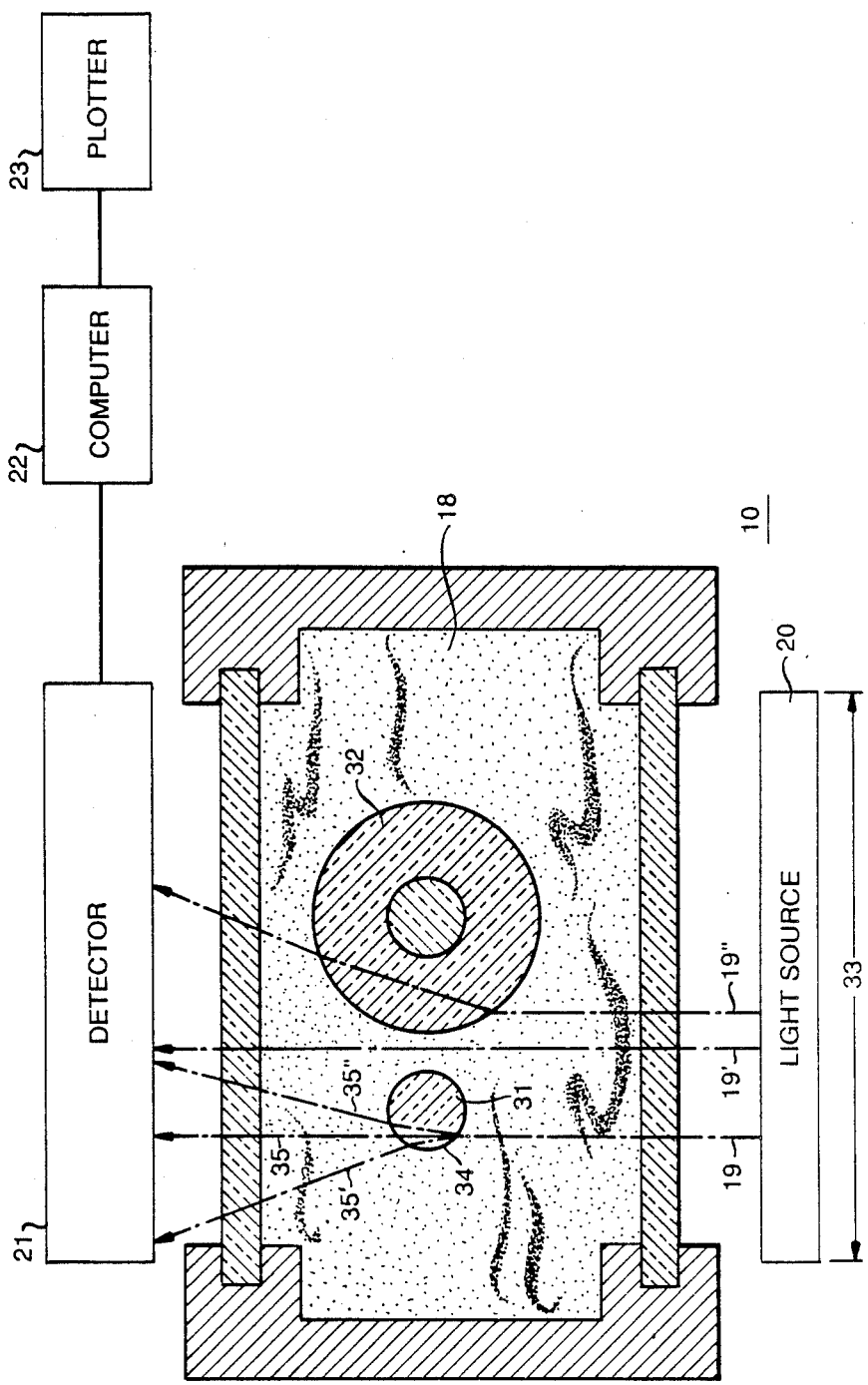
FIG. 6—top schematic representation of the apparatus of the invention for profiling the refractive index of a translucent body.

The preferred embodiment of the herein disclosed invention circumvents the foregoing problems. Referring to FIG. 6, a fused silica rod 31 is suspended in index matching oil 18 by a support (not shown). The longitudinal axis of rod 31 is contained in the same plane as the longitudinal axis of unclad tube 32, which plane is perpendicular to light beam 19 and parallel to scan axis 33 of light beam 19.

At the start of the scan of monochromatic light beam 19, which is typically a two milliwatt helium neon laser, along scan axis 33, beam 19 goes through at least part of rod 31. Light beam 19 is focused at the axis of tube 32 as described in U.S. Pat. No. 4,726,677 to Werner J. Glantschnig et al (incorporated by reference herein). If the refractive index of oil 18 happens to match that of rod 31, beam 19 will not be refracted at surface 34 as shown by beam 35 exiting rod 31. On the other hand, if there is an index mismatch, between oil 18 and rod 31, beam 19 will be slightly refracted either toward or away from the normal to surface 34 of rod 31 as shown by beams 35' and 35''. At any rate, if beam 19 is refracted at surface 34, as can be established by comparing the measurements obtained with beam 19 passing through both rod 31 and oil 18 with measurement 19' taken with beam 19 passing through only oil 18, the index difference between oil 18 and rod 31, and hence between the index matching oil and silica, can be computed. Once this difference is known, the problem is solved. The refractive index profile of unclad transparent body 32 can be plotted with the proper offset so that the index profile of body 32 is referenced to the index of silica rather than that of index matching oil 18.

The diameter of silica rod 31 should be large enough to permit several hundred data points to be measured as light beam 19 is scanned across it. In the preferred embodiment, a one-half inch diameter rod 31 was used effectively. As the data points were spaced only twenty microns apart, approximately eight hundred measurements can be taken to assure that an accurate profile is constructed. In addition, Snell's Law, upon which the refractive angle computations of computer 22 are based, presupposes surface 34 to be flat compared with the width of light beam 19. Beam 19 is approximately fifty microns wide so that surface 34 of one-half inch rod 31 is, for all practical pruposes, flat.

It was also determined that, although not critical, a one-quarter inch spacing between rod 31 and transparent body 32 was adequate if there is not too large a refractive index mismatch between silica rod 31 and oil 18. This spacing should be large enough to avoid interference between beam 19 exiting rod 31 and body 32, and vice-versa.

It was also found preferable, that while computer 22 is calculating the offset to be used in plotting the refractive index of body 32, that the scan of beam 19 be stalled in the gap between rod 31 and body 32. Of course, this was a matter of choice rather than necessity.

Figure 7:
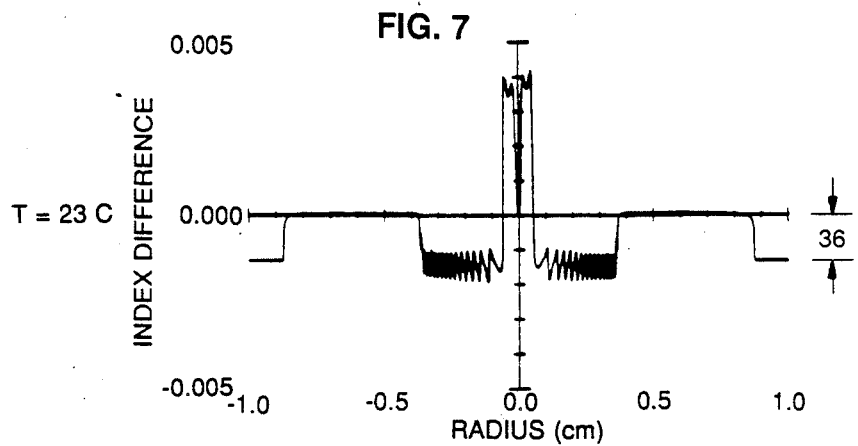
FIGS. 7, 11 and 12—refractive index profiles of a clad single mode preform at three different temperatures using the method and apparatus of this invention.
Figure 11:
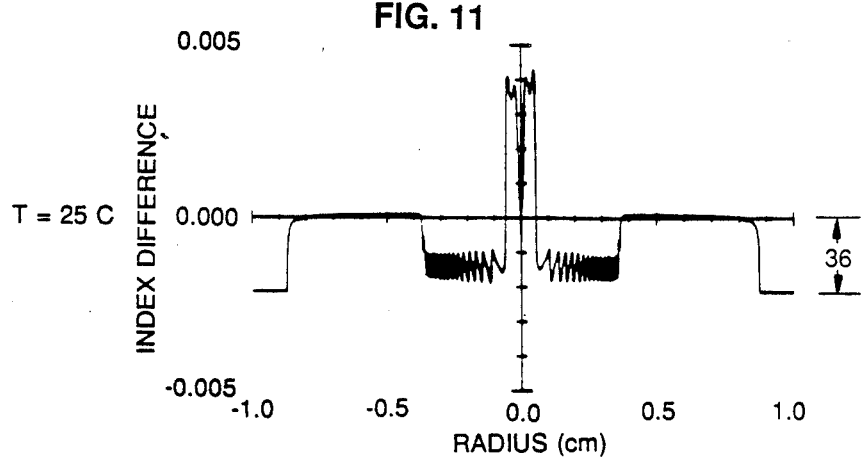
Figure 12:
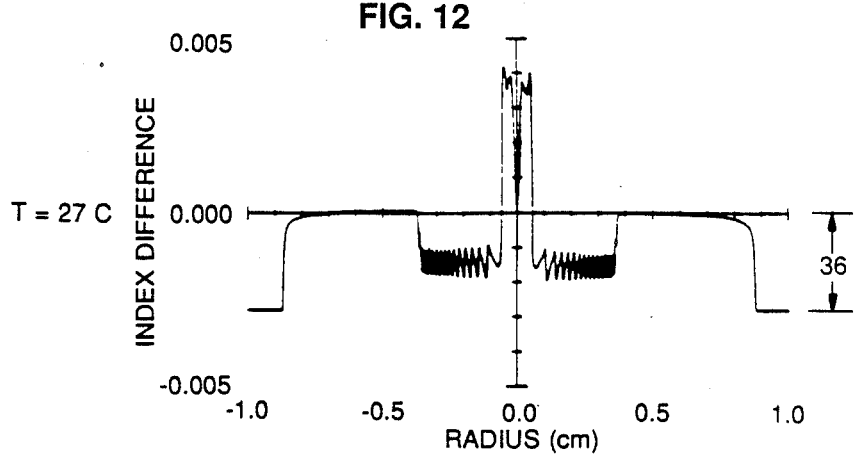

Referring to FIGS. 7, 11 and 12, in order to check the effectiveness of this invention, index matching oil 18 was heated, and while it was cooling down and its index of refraction increasing, a standard MCVD single mode fiber preform with a silica cladding was profiled three times using the method and apparatus of this invention. During the measurements, nothing was assumed about the composition of the preform. The invention was being checked to see if it would be able to determine the proper index offset such that the silica cladding would fall on the zero index reference line in the profile plot. The results of this check are shown in FIGS. 7, 11 and 12. Even though the mismatch 36 between the oil and the silica was different for each temperature, the profiler of this invention automatically determined the correct index offset in each case.

Figure 8:
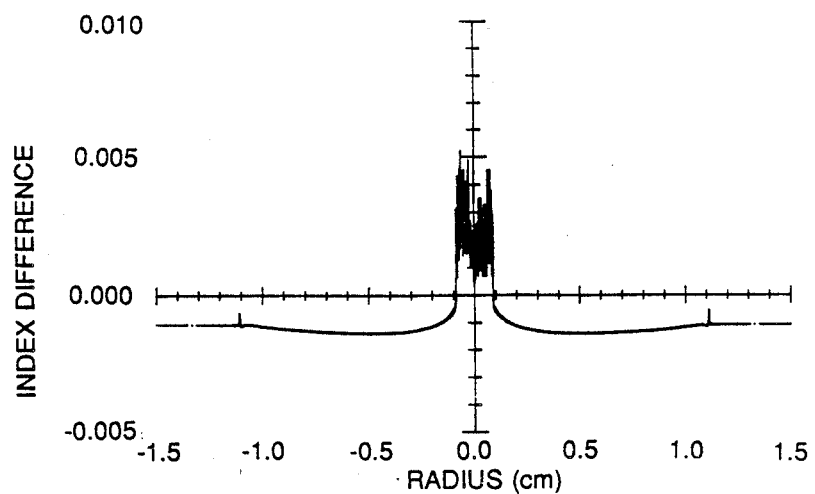
FIG. 8—refractive index profile of an unclad preform using the apparatus and method of this invention.
Figure 9:
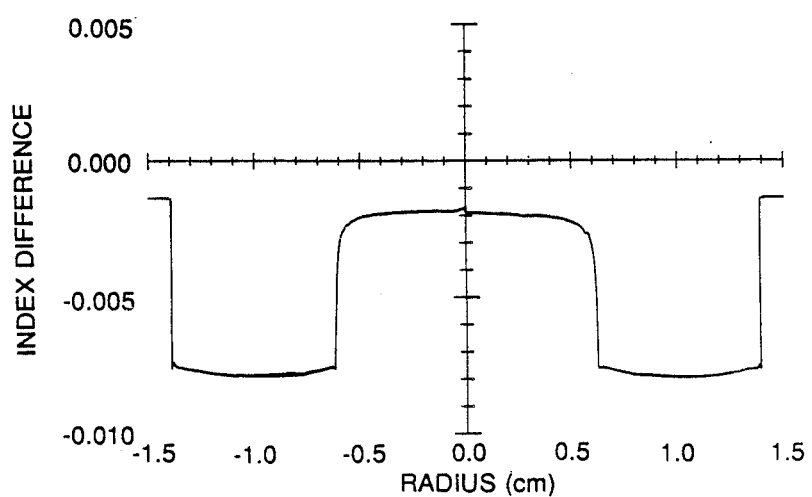
FIG. 9—refractive index profile of a fluorinated tube.

FIGS. 8 and 9 show profile measurements obtained with the present invention for objects which could not have been properly and efficiently profiled without this invention. FIG. 8 is the profile of an unclad preform made with the OVD process. It has a fluorinated cladding extending all the way to its surface. Prior to this invention, it would have been necessary to have collapsed a silica jacket over this preform in order to obtain an accurate profile of the index depression of the fluorinated clad referenced to the index of silica, the zero line in the profile.

FIG. 9 is the profile of a fluorinated tube made with the OVD process. Again, the measure of its index depression relative to the index of silica could not have been determined by nondestructive prior art methods or apparatus.

Figure 10:
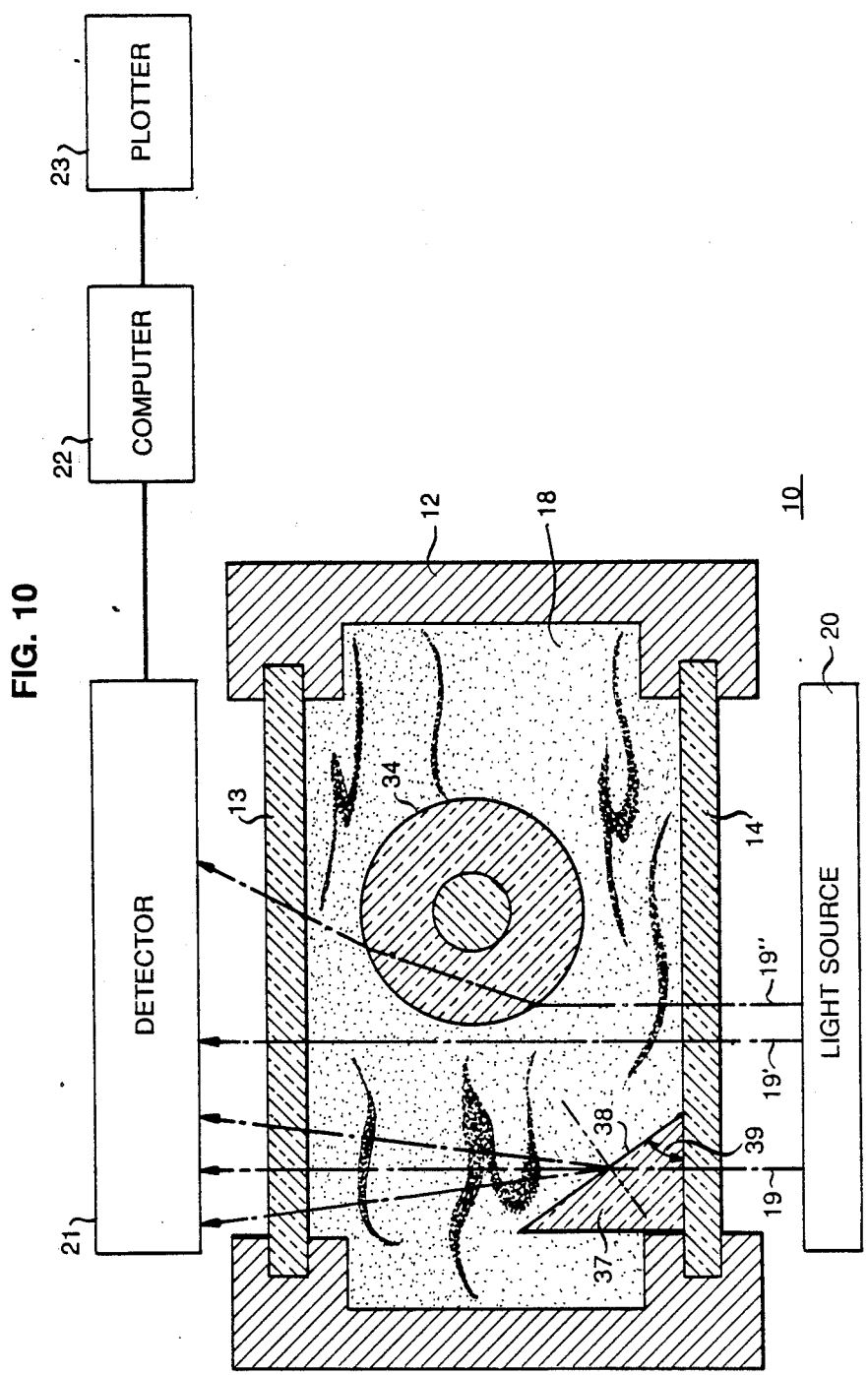
FIG. 10—block schematic representation of an alternative apparatus of the invention for profiling the refractive index of a translucent body.

Alternatively, referring to FIG. 10, instead of a rod, a fused silica prism 37 is cemented to the inside of window 14 using UV curable epoxy. The epoxy was selected to be compatible with the oil so as not to deteriorate over time. The selection was made with the aid of R. P. Cargille Laboratories, Inc. of Cedar Grove, N.J., the supplier of index matching oil 18.

Surface 38 of prism 37 in this embodiment performs the same function as does surface 34 of rod 31 in the preferred embodiment. However, it was found that as angle 39 increased, the deflection of light beam 19 increased providing a greater deflection for a given index mismatch between oil 18 and silica. The greater prism angle 39, the greater the accuracy of the profile obtained. However, as rod 31 in effect provides an infinite range of angles, the accuracy of the profiles obtained using rod 31 instead of prism 37 were as much as an order of magnitude more accurate. Other modifications and embodiments may be made by those skilled in the art without departing from the spirit or scope of the invention.

I claim:

1. A method of nondestructively determining the refractive index of a translucent body, comprising the steps of:
   scanning a light beam across at least a portion of the surfaces of the translucent body and a translucent reference;
   detecting the refraction angles of the light beams exiting both the translucent body and the reference; and
   comparing the detected refraction angle data thereby determining the refractive index profile of the translucent body relative to the translucent reference.

2. The method of claim 1 in which the transparent body is an unclad preform.

3. The method of claim 1 in which the transparent body is an unclad tube.

4. The method of claim 1 in which the light beam is a narrow beam of monochromatic light scanned substantially perpendicular to an imaginary plane containing the longitudinal axis of the translucent body.

5. The method of claim 1 in which the translucent body and the translucent reference are immersed in index matching fluid and further includes the step of preprocessing the detected refraction angle data to correct the data for effects arising from an index mismatch between the fluid and the reference.

6. The method of claim 1 in which the reference is a silica angle prism.

7. The method of claim 1 in which the reference is a silica rod mounted with its longitudinal axis in a plane containing the longitudinal axis of the translucent body, which plane is substantially perpendicular to the light beam.

8. Apparatus for nondestructively determining the refractive index of a translucent body, comprising:
   means for scanning a light beam across at least a portion of the surfaces of the translucent body and a translucent reference,
   means for detecting the refraction angles of the scanning beam exiting both the translucent body and the reference; and
   means for comparing the detected refraction angle data thereby determining the refractive index profile of the translucent body relative to the translucent reference.

9. The apparatus of claim 8 in which the translucent body is an unclad preform.

10. The apparatus of claim 8 in which the translucent body is an unclad tube.

11. The apparatus of claim 8 in which the light beam is a narrow beam of monochromatic light scanned in a plane perpendicular to a plane containing the longitudinal axis of the translucent body.

12. The apparatus of claim 8 which includes:
means for immersing both objects in index matching fluid; and
means for preprocessing the detected angle data to correct for the effects arising from an index mismatch between the refractive indexes of the fluid and the reference.

13. The apparatus of claim 8 in which the reference is a silica angle prism.

14. The apparatus of claim 8 in which the reference is a silica rod mounted with its longitudinal axis in a plane containing the longitudinal axis of the translucent body, which plane is substantially perpendicular to the scanning light beam.

* * * * *